United States Patent [19]

Kirkpatrick

[11] 4,339,382
[45] Jul. 13, 1982

[54] PROCESS FOR MANUFACTURING N-ARYLTHIOCARBAMOYL-2-AMINO-1H-ISOINDOLE-1,3-(2H)DIONES

[75] Inventor: Joel L. Kirkpatrick, Washington Crossing, Pa.

[73] Assignee: Gulf Oil Corporation, Pittsburgh, Pa.

[21] Appl. No.: 115,528

[22] Filed: Feb. 11, 1980

[51] Int. Cl.³ .......................................... C07D 209/48
[52] U.S. Cl. ................................... 548/474; 548/475
[58] Field of Search ................................... 260/326 S

[56] References Cited

U.S. PATENT DOCUMENTS

| 4,264,502 | 4/1981 | Patel et al. ........................... 71/96 |
| 4,289,527 | 9/1981 | Hedrich ........................... 260/326 S |
| 4,292,071 | 9/1981 | Kirkpatrick ........................... 260/326 S |

OTHER PUBLICATIONS

Sykes, "A Guide Book to Mechanisms in Organic Chem." (1966), pp. 72-25, 77.
Gould, "Mechanism & Structure in Organic Chem." (1959), Chapter 8, pp. 251-254, 268-269.
Buehler & Pearson, "Survey of Organic Synthesis" (1970), pp. 897-899, 907.

*Primary Examiner*—Mark L. Berch
*Attorney, Agent, or Firm*—Deane E. Keith; Forrest D. Stine

[57] ABSTRACT

In the manufacture of N-aryl or alkylthiocarbamoyl-2-amino-1H-isoindole-1,3-(2H)diones of the type represented by the structural formula

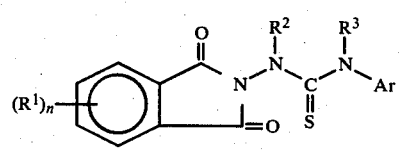

by ring closure of a corresponding ortho-carbonyl substituted benzoylhydrazine thiocarboxamide, greatly improved yields are obtained by cyclization of a compound of the structural formula:

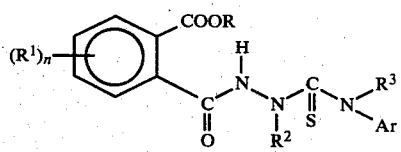

by reaction under mildly basic conditions at ambient or room temperature in the presence of a non-reactive polar organic solvent and a hindered aliphatic amine.

4 Claims, No Drawings

PROCESS FOR MANUFACTURING N-ARYLTHIOCARBAMOYL-2-AMINO-1H-ISOINDOLE-1,3-(2H)DIONES

DESCRIPTION OF THE INVENTION

A novel class of compounds which are useful as plant growth regulators, having the general structural formula:

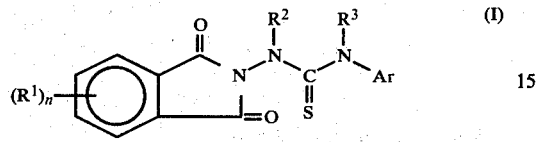

in which

R$^1$ is; C$_1$ to C$_4$ alkyl, nitro, chloro or fluoro and n is zero or an integer from 1 to 4.

R$^2$ and R$^3$ are; H or C$_1$ to C$_4$ alkyl and

Ar is; naphthyl, phenyl or phenyl bearing one or more substituents of the group C$_1$ to C$_4$ alkyl, C$_1$ to C$_4$ alkoxycarbonyl, bromo, chloro and trifluoromethyl, is disclosed by Patel and Rutter in U.S. Patent application Ser. No. 19,065, abandoned. Various methods may be used to manufacture the novel compounds. Because of the variety of chemical structures within the class of compounds, however, no single method of synthesis has been found to give high yields of all members of the class.

Among methods by which the compounds of formula (I) may be made are the following:

1. Reacting a compound of the formula

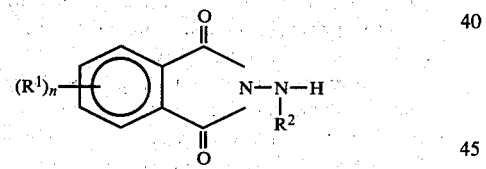

in a mutual solvent with a compound of the formula

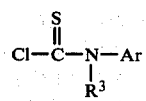

in the presence of an acid acceptor or with a compound of the formula SCN—Ar.

2. Reacting a compound of the formula

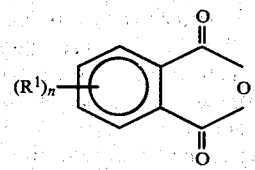

with a compound of the formula

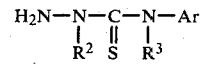

in a mutual solvent.

3. Reacting a compound of the formula

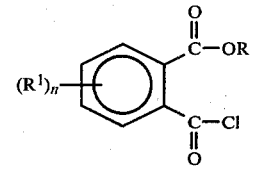

with a compound of the formula

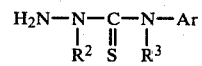

in a mutual solvent in the presence of an acid acceptor.

In the methods outlined above, variation in the substituent groups R$^1$ and R$^3$ may in some instances greatly affect the driving force on the desired reaction. Some of the reactions may be operated in specific instances with yields of 50 percent or better at room temperature or below, depending principally upon the nature of these two substituents. All of the above methods are useful but none can be considered a general procedure which is equally desirable for manufacture of all of the compounds of formula (I).

A general method of manufacturing the compounds of formula (I) is the ring closure of a compound of the formula

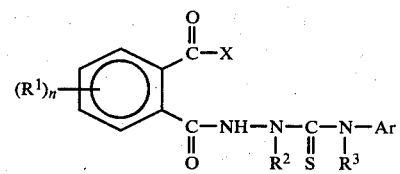

in which X represents a good leaving group in which an electronegative atom is attached to the carbon atom of the carbonyl structure. For example, X may represent a group —OR or —SR of an ester or thioester or an —OH or —SH structure of an acid or thio acid, or a group —O—CO—R of a mixed anhydride. The attachment of X may change or be a transitory event in the course of a ring closure reaction, as when X is originally —OH and an acid anhydride is used as a dehydrating reagent to promote ring closure. When X is other than —OH, basic catalysts (organic or inorganic) or heat alone may be sufficient to effect ring closure. When X is —OH, use of dehydrating reagents is preferred to promote ring closure. A generally useful laboratory method involves the ring closure step illustrated below:

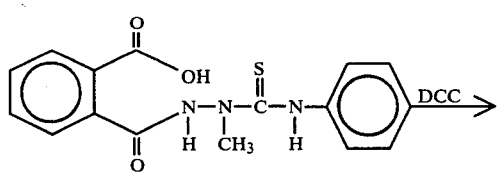

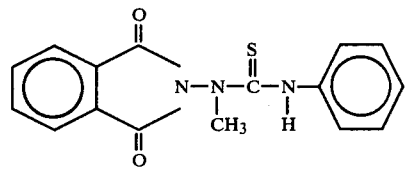

In a typical example, the above reaction is performed at low temperature, (about 2°-5° C.) in the presence of N,N¹—dicyclohexylcarbodiimide and allowed to warm up to room temperature on standing. Yields may be as high as about 60 percent, but in some instances are much lower.

I have discovered that in the manufacture of N-(aryl or alkylthiocarbamoyl)-2-amino-1H-isoindole-1,3-(2H)diones of the type represented by the formula

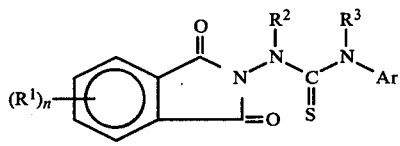

of a corresponding ortho-carbonyl substituted benzoyl-hydrazine thiocarboxamide, greatly improved yields are obtained by cyclization of a corresponding ortho-carbo-($C_1$-$C_4$) alkoxybenzoyl hydrazinethiocarboxamide under very mild basic conditions in the presence of a non-reactive polar organic solvent and a reaction-promoting amount of a hindered aliphatic amine.

The operation of the improved method of manufacture is illustrated by means of the following specific examples.

EXAMPLE 1

To a solution of 3.0 g (0.0087 mole) of 2-(o-carbomethoxybenzoyl)-1-methyl-N-phenylhydrazinethiocarboxamide in 75 ml of tetrahydrofuran, was added 0.065 g (0.00087 mole) of tert.butylamine and the reaction was allowed to stir at room temperature for 16 hours. The solvent was removed under reduced pressure and the yellow residue was dissolved in a small amount of acetone and the product precipitated with dil. hydrochloric acid. The resulting solid was collected, stirred in water, filtered and dried to give 2.4 g (88%) of N-Methyl-N-(phenylthiocarbamoyl)-2-amino-1H-isoindole-1,3-(2H)dione, m.p. 150°-53°.

EXAMPLES 2-7

The foregoing procedure was repeated with various ortho-carbarboalkoxybenzoyl hydrazinethiocarboxamides according to the following scheme:

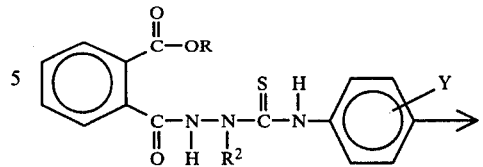

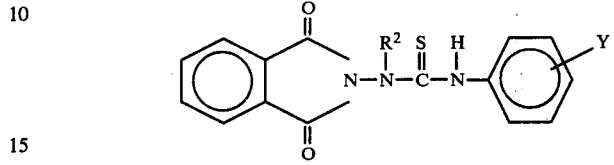

Results are tabulated below.

| Example | R | $R^2$ | Y | Yield |
|---|---|---|---|---|
| 2 | $CH_3$ | $CH_3$ | H | 95% |
| 3 | $C_2H_5$ | $CH_3$ | H | good(by NMR-not isolated) |
| 4 | $n-C_4H_9$ | $CH_3$ | H | >75%(by NMR-not isolated) |
| 5 | $CH_3$ | benzyl | H | ~100% |
| 6 | $CH_3$ | $CH_3$ | 2,6-di$CH_3$ | 75% |
| 7 | $CH_3$ | H | 3-Cl | 95% |

The success of the improved method depends upon avoidance of competing reactions which may occur if the specified conditions are not complied with. In general, the method can be operated within the limits of ambient daytime temperatures. However, at temperatures in excess of 50° C. a different reaction occurs, with the release of an aryl isothiocyanate by-product. For best results, room temperature, that is, the temperature of rooms for human habitation, is preferred.

The solvent should be polar, so that the amine employed to promote the reaction can produce the desired mildly basic conditions. However, the solvent should be non-reactive in the system. Alcohols, for example, are unsuitable and dimethoxyethane yields impure products. Solvents which have proved to be acceptable are ethyl acetate, toluene, acetone and tetrahydrofuran.

The amine should have sufficient basic strength to promote the ring closure. However, an unhindered primary or secondary basic amine will compete with the amide nitrogen in the starting material to prevent ring closure. For example, piperidine and n-propylamine react to give the corresponding amides, thus effectively preventing the ring closure. No reaction is observed with pyridine. Examples of suitable amines are tert.butyamine, diisopropylamine, triethylamine, 1,4-diazabicyclo[2,2,2] octane and isopropylamine. The structures of these are hindered with respect to amide formation as a competing reaction.

Among the suitable reaction solvents and hindered aliphatic amines, certain combinations are more desirable than others. For example, use of tert.butylamine is preferred with acetone, ethyl acetate or tetrahydrofuran as solvent and acetone is the preferred solvent for use with triethylamine.

The following example is illustrative of a procedure employing larger quantities of reagents and with acetone as a reaction solvent.

EXAMPLE 8

The following were charged to a five-liter reaction flask:
1000 ml. of acetone,
280 g. of 2-(o-carbomethoxybenzoyl)-1-methyl-N-phenylhydrazinethiocarboxamide and
8.6 ml. of tert.butylamine.

Complete solution was obtained in about 20 minutes. The mixture was then allowed to stir at room temperature overnight. At the end of this time, some solid was visible in the reactor. Two liters of water were added causing the temperature to rise to 35° C. The reaction mixture was then cooled to 10° C. and the solid product was collected by filtration. The product was washed on the filter with water, then with isopropyl alcohol, then again with water and was dried in an oven at 50° C. There was obtained 213.1 g of product (84% yield), m.p. 155°–156° C. d.

The carbomethoxybenzoyl thiosemicarbazide starting material for the present process may be obtained conveniently by reacting the corresponding methyl phthaloyl chloride with a suitable thiosemicarbazide. Both of these reagents may be made by conventional methods. Below is an illustrative procedure.

Synthesis of 2-(o-carbomethoxybenzoyl)-1-methyl-N-phenyl hydrazinethiocarboxamide A solution of 45.3 g (0.25 mole) of 1-methyl-N-phenylhydrazinecarboxamide and 19.8 g (0.25 mole) of pyridine in 800 ml of 1,2-dimethoxyethane was stirred at room temperature while 49.8 g (0.25 mole) of methyl phthaloyl chloride in 100 ml of 1,2-dimethoxyethane was added dropwise over a period of two hours. The resulting reaction mixture was stirred for 16 hours at room temperature. At the end of this time the contents of the flask were poured into ice water. The solid which formed was collected and amounted to 73.3 g (85%); the melting point was 153.5°–154°.

In some instances, if the reaction time in the above procedure is prolonged, ring closure also occurs, to give good yields of the desired final product. However, the method is not equally satisfactory for all of the compounds of the class. It is also possible to effect ring closure of the product of the above procedure under strongly basic conditions, as in ethanolic sodium hydroxide, but with much lower yields of the desired product.

The improved method of the present invention is a general method which is not limited to manufacturing only the compounds which fall within the strict limitations which have been previously disclosed. The nature of the substituent groups, which may be critical with respect to the characteristics of the desired compounds, is not particularly critical with regard to operability of the improved synthesis method. In general, the method is applicable to manufacture of compounds having the general structural formula:

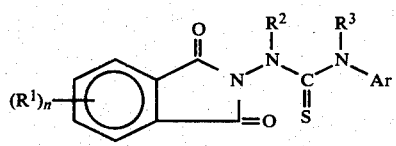

in which $R^1$ is; $C_1$ to $C_4$ alkyl or alkoxy, nitor, cyano or halo and n is zero or an integer from 1 to 4.

$R^2$ and $R^3$ are; H or $C_1$ to $C_4$ alkyl or benzyl and

Ar is; naphthyl, adamantyl, benzyl, alkyl, phenyl or phenyl bearing one or more substituents of the group $C_1$ to $C_4$ alkyl, $C_1$ to $C_4$ alkoxycarbonyl, bromo, chloro and trifluoromethyl.

By selection of suitable amines and solvents a skilled chemist will be able to employ the improved method of ring closure to make a great variety of isoindoledione compounds.

I claim:

1. In the method of manufacturing compounds having the general structural formula:

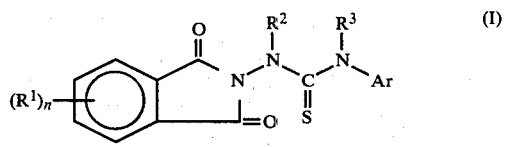

in which $R^1$ is $C_1$ to $C_4$ alkyl or alkoxy, nitro, cyano or halo and n is zero or an integer from 1 to 4;

$R^2$ and $R^3$ are H or $C_1$ to $C_4$ alkyl or benzyl and

Ar is naphthyl, adamantyl, benzyl, alkyl, phenyl or phenyl bearing one or more substituents of the group $C_1$ to $C_4$ alkyl, $C_1$ to $C_4$ alkoxycarbonyl, bromo, chloro and trifluoromethyl by ring closure of a compound having the corresponding structural formula

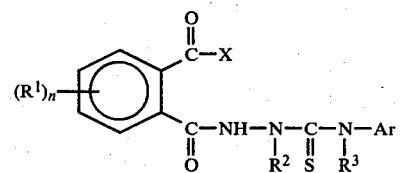

in which X represents a good leaving group, in which an electronegative atom is attached to the carbon atom of the carbonyl structure; the improvement comprising cyclization of a compound of the corresponding structural formula

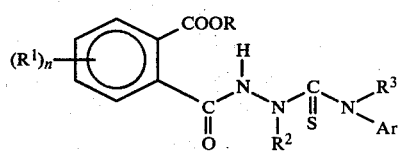

in which R is $C_1$ to $C_4$ alkyl by reaction under mildly basic conditions at a temperature below 50° C. in the presence of a non-reactive polar organic solvent and a hindered aliphatic amine.

2. The improved method of claim 1 in which R is methyl, the solvent is acetone, ethyl acetate or tetrahydrofuran, the amine is tert.butylamine and the cyclization is performed at room temperature.

3. The improved method of claim 1 in which R is methyl or ethyl, the solvent is tetrahydrofuran, the amine is tert.butylamine and the cyclization is performed at room temperature.

4. The improved method of claim 1 in which R is methyl, the solvent is acetone, the amine is tert.butylamine and the cyclization is performed at room temperature.

* * * * *